United States Patent
Urankar et al.

(10) Patent No.: US 9,448,175 B2
(45) Date of Patent: Sep. 20, 2016

(54) METHOD FOR COMPENSATING FOR THE AGING OF A REAGENT DURING FLUORESCENCE MEASUREMENTS CARRIED OUT ON PARTICLES, AND BIOLOGICAL ANALYSIS DEVICE IMPLEMENTING THE METHOD

(71) Applicant: HORIBA ABX SAS, Montpellier (FR)

(72) Inventors: Alexandra Urankar, Saint Clement de Riviere (FR); Philippe Nerin, Montpellier (FR); Moustapha Hariche, Combaillaux (FR); Gilles Cauet, Fontanès (FR)

(73) Assignee: HORIBA ABX SAS, Montpellier (FR)

( * ) Notice: Subject to any disclaimer, the term of this patent is extended or adjusted under 35 U.S.C. 154(b) by 0 days.

(21) Appl. No.: 14/423,030

(22) PCT Filed: Aug. 19, 2013

(86) PCT No.: PCT/EP2013/067251
§ 371 (c)(1),
(2) Date: Feb. 20, 2015

(87) PCT Pub. No.: WO2014/029743
PCT Pub. Date: Feb. 27, 2014

(65) Prior Publication Data
US 2015/0241352 A1    Aug. 27, 2015

(30) Foreign Application Priority Data

Aug. 21, 2012 (FR) ...................... 12 57905

(51) Int. Cl.
*G01N 21/64* (2006.01)
*G01N 21/27* (2006.01)
*G01N 15/14* (2006.01)
*G01N 33/49* (2006.01)
*G01N 35/00* (2006.01)
*G01N 15/10* (2006.01)

(52) U.S. Cl.
CPC ........ *G01N 21/6486* (2013.01); *G01N 15/147* (2013.01); *G01N 21/274* (2013.01); *G01N 21/6428* (2013.01); *G01N 33/49* (2013.01); *G01N 35/00663* (2013.01); *G01N 2015/1006* (2013.01); *G01N 2035/00673* (2013.01); *G01N 2201/121* (2013.01)

(58) Field of Classification Search
None
See application file for complete search history.

(56) References Cited
PUBLICATIONS

Hulspas et al: "Flow cytometry and the stability of phycoerythrin-tanden dye conjugates", Cytometry Part A, vol. 75A, No. 11, Sep. 23, 2009, pp. 966-972, XP055062054, ISSN: 1552-4922, DOI: 10.1002/cyto.a.20799.*
BD Biosciences, "An Introduction to Compensation for Multicolor Assays on Digital Flow Cytometers," Aug. 2009, pp. 1-12.

* cited by examiner

*Primary Examiner* — David Porta
*Assistant Examiner* — Hugh H Maupin
(74) *Attorney, Agent, or Firm* — Arent Fox LLP (57) ABSTRACT

The present invention relates to a method for compensating for the breakdown of a reagent stored in an aqueous phase comprising at least one fluorescent compound and enabling the identification of particles, including the steps of: (i) measuring the fluorescence level FLUOm(t) of particles marked with said reagent; (ii) measuring the absorbance at at least one wavelength of a solution of said reagent, at a time t close to the time of said fluorescence level FLUOm(t) measurements, so as to determine at least one current optical density DO(t) of the reagent; and (iii) calculating a correction of the fluorescent level measurements using said at least one current optical density DO(t) and at least one initial optical density DO(0) of the reagent that has not been broken down. The invention also relates to a biological analysis device implementing the method.

11 Claims, 4 Drawing Sheets

METHOD FOR COMPENSATING FOR THE AGING OF A REAGENT DURING FLUORESCENCE MEASUREMENTS CARRIED OUT ON PARTICLES, AND BIOLOGICAL ANALYSIS DEVICE IMPLEMENTING THE METHOD

CROSS-REFERENCE TO RELATED APPLICATIONS

This application is the U.S. National Phase of International Patent Application No. PCT/EP2013/067251, filed Aug. 19, 2013, which claims priority to FR 1257905, filed Aug. 21, 2012, the contents of each are hereby incorporated by reference in their entireties.

TECHNICAL FIELD

The present invention relates to a method for compensating for the degradation over time of a fluorescent reagent during fluorescence measurements carried out on particles, including cells labeled with this reagent.

The field of the invention is more particularly, but not exhaustively, that of biological analysis devices, and in particular that of hematology devices.

PRIOR ART

Cellular analysis, and notably blood cell analysis, require the use of specific reagents allowing preliminary chemical treatment of the sample. Various physicochemical functions are performed such as dilution, staining or selective destruction of certain cellular populations (differential lysis).

These reagents are packaged in containers suitable for use in analysis equipment such as automatic hematology analyzers or flow cytometers. It is usual to give each reagent a single chemical function, but the current tendency is to give several functions to one and the same reagent from considerations of cost or of simplicity of use. Simplicity of maintenance both for the manufacturer of the product and for the user is also a desirable aim.

There are nevertheless difficulties when we wish to manufacture a single reagent offering several simultaneous physicochemical functions: the various chemical compounds of the reagent may react with one another, to give rise to byproducts whose physicochemical functions differ markedly from the original products. This change or degradation may alter the preliminary treatment of the sample, notably blood, and may be reflected in an incorrect analysis result.

The change or degradation of the reagent may also depend on environmental factors such as, for example, temperature or electromagnetic radiation. In particular, certain fluorescent compounds used in reagents degrade in an aqueous phase, with a rate of degradation that depends on the temperature. This is notably the case with Thiazole Orange (TO), which is a fluorescent compound used as a stain for cellular components and is intended to become attached to the intracellular DNA or RNA.

Reagents comprising fluorescent compounds such as TO are notably described in document FR 2 821 428. They may be used in hematology systems, as described for example in document WO 2006/024716. Degradation of the fluorescent compounds of the reagent leads to a decrease in the fluorescence levels, which may cause errors in counting and classification of the cells analyzed.

Decomposition (or photodecomposition) of the heterocyclic polymethines, which include TO, in the presence of molecular oxygen is known. The presence of a powerful oxidizing agent such as hydrogen peroxide also leads to degradation of TO with formation of one of the degradation products identified, benzothiazolone. However, degradation of TO occurs even in the absence of light, and addition of antioxidants or replacement of the dissolved oxygen with an inert gas such as argon does not slow this degradation. It appears that the degradation of TO in hematology reagents results from spontaneous hydrolysis of the molecule.

Certain reagents are formulated so as to limit or at least slow this degradation, for example those described in document U.S. Pat. No. 7,638,290. However, this is not sufficient to guarantee good stability of the compounds over time.

To prevent or inhibit the phenomenon of change or degradation in an aqueous medium, fluorescent compounds may be stored in an organic solvent in highly concentrated form and diluted at the time of the measurements, as described for example in document EP 2 175 340. In fact, in an organic solvent such as an alcohol or ethylene glycol, change or degradation of the fluorescent compound is almost nonexistent, which is a real advantage relative to an aqueous solvent.

However, this manner of proceeding has other drawbacks. It is necessary to employ a larger number of containers actually within the analyzer, which also leads to a higher charge for management of the number of products within the analytical laboratory or the hematology laboratory.

Moreover, when a chemical reagent has to be reconstituted before use, actually within the analyzer or in a device placed alongside, the complexity of use is also increased since, ultimately, it is necessary to undertake the mixing of two or more liquids, whose viscosities are not always the same. This may create problems of homogeneity of the product, which may lead to poor treatment of the sample. A mixer with more or less perfect efficiency must be used, which leads to an extra cost and an increased risk of breakdown.

One aim of the present invention is to propose a method for measuring or at least evaluating the aging of a reagent.

Another aim of the present invention is to propose a method for compensating for the errors of fluorescence measurement due to the aging of a reagent.

Another aim of the present invention is to prolong the shelf life of the reagents used.

Another aim of the present invention is to propose a marker representative of the temperature to which the reagent has been exposed during its life, including during transport if applicable.

DISCLOSURE OF THE INVENTION

These aims are achieved with a method for compensating for the degradation of a reagent stored in an aqueous phase comprising at least one fluorescent compound and allowing identification of particles, comprising a step of measurement of the fluorescence level $FLUOm(t)$ on particles labeled with said reagent, characterized in that it further comprises steps of:
  carrying out absorbance measurements at at least one wavelength on a solution of said reagent, at a time point t close to that of said measurements of the fluorescence level $FLUOm(t)$, so as to determine at least one current optical density $OD(t)$ of the reagent, and,
  calculating a correction of the measurements of the fluorescence level using said current optical density or densities $OD(t)$ and at least one initial optical density $OD(0)$ of the degradation-free reagent.

According to embodiments:
the degradation-free reagent may be such as at the end of production;
absorbance measurements may be performed at at least one wavelength corresponding to an absorption peak of a fluorescent compound;
the particles may be such as cells or may comprise cells.

The reagent may notably comprise:
at least one fluorescent compound of the polymethine type,
Thiazole Orange.

According to embodiments, the method according to the invention may comprise steps of:
calculating a ratio K(t) corresponding to the ratio of an initial optical density OD(0) to a current optical density OD(t), and
calculating corrected fluorescence levels FLUOc(t) by multiplying the fluorescence levels FLUOm(t) measured around the measurement time point t on particles labeled with the reagent, by the ratio K(t).

The method according to the invention may further comprise steps of:
measuring initial optical densities ODi(0) and current optical densities ODi(t) at several wavelengths $\lambda i$ (corresponding for example to the absorption peaks of fluorescent compounds),
calculating ratios Ki(t) at said wavelengths $\lambda i$, and
calculating corrected fluorescence levels FLUOci(t) at said wavelengths $\lambda i$.

According to other embodiments, the method according to the invention may further comprise steps of:
determining beforehand a model of degradation establishing a relation between changes in fluorescence level $\Delta$FLUO on reference particles and changes in the optical density of the reagent $\Delta$OD due to its degradation, and
calculating a number of lost fluorescence channels CP(t), from measurements of current optical density OD(t), from measurements of initial optical density OD(0), and from said model of degradation.

The method according to the invention may further comprise steps of:
determining beforehand a model of degradation in the form of a coefficient $\alpha$ corresponding to a ratio of the changes in fluorescence level $\Delta$FLUO to changes in optical density of the reagent $\Delta$OD,
calculating a number of lost fluorescence channels CP(t), in the form of a difference between the current optical density OD(t) and the initial optical density OD(0), multiplied by the coefficient $\alpha$,
determining a reference fluorescence value <FLUO(t)> statistically representative of the measured fluorescence levels FLUOm(t),
calculating a corrective gain GC(t) corresponding to a reference fluorescence value <FLUO(t)> divided by a difference between said reference fluorescence value <FLUO(t)> and the number of lost fluorescence channels CP(t), and
calculating corrected fluorescence levels FLUOc(t) by multiplying the fluorescence levels FLUOm(t) measured at a measurement time point t on particles labeled with the reagent, by the corrective gain GC(t).

The method according to the invention may further comprise determination of a plurality of models of degradation from measurements of optical density at several wavelengths.

According to another aspect, a device for cellular analysis by flow cytometry is proposed, comprising means for fluorescence level measurement on particles labeled with a reagent, characterized in that it further comprises:
means for performing absorbance measurements at at least one wavelength on a solution of said reagent, at a time point t close to that of said measurements of the fluorescence level, so as to determine at least one current optical density OD(t) of the reagent, and
calculating means, capable of calculating a correction of the measurements of the fluorescence level using said current optical density or densities OD(t) and at least one initial optical density OD(0) of the degradation-free reagent.

According to embodiments, the device according to the invention may comprise a cell for measurement by spectrophotometry.

The cell for measurement by spectrophotometry may comprise a polychromatic light source and a photoreceptor provided with an optical filtering system allowing measurement of the optical densities at the various central wavelengths $\lambda i$.

According to embodiments, the device according to the invention may further comprise a hematology analyzer.

Thus, the method according to the invention offers a certain number of advantages, such as:
prolonging the shelf life of the reagents used,
reducing the number and amount of products to be supplied in the laboratory,
the possibility of making analysis systems that are more compact, with a simplified fluidic system, without reagent mixer or conditioner within the analyzer,
reduced risk of breakdown,
more attractive cost prices and operating costs.

DESCRIPTION OF THE FIGURES AND EMBODIMENTS

Other advantages and particular features of the invention will become clear on reading the detailed description of implementations and embodiments that are not in any way limiting, and the following appended drawings:

FIG. 2 illustrates the absorption spectrum of TO (FIG. 2a), and the absorption spectra of the hydrolysis products (FIGS. 2b and 2c), FIG. 3 illustrates the evolution of the fluorescence measurements obtained with TO on granulocytes, respectively 7 weeks (FIG. 3a) and 16 months (FIG. 3b) after production of the reagent.

An embodiment of the method according to the invention will now be described, applied to a reagent comprising a fluorescent compound, Thiazole Orange (TO), stored in aqueous solution, use of which is described for example in document WO 2006/024716.

This embodiment is not in any way limiting, and the invention may of course be applied to other reagents comprising for example several staining agents.

As explained above, the invention makes it possible to prolong the shelf life of the reagents. In the embodiment described, the use of the model for correcting the intensity of the fluorescence makes it possible to prolong the duration of use of the reagent by several months, which may thus be extended from six to nine months, or even to twelve months without degradation of analytical performance. The expiry date of the reagents used in the analyzers is therefore prolonged by that much.

Figure 1:
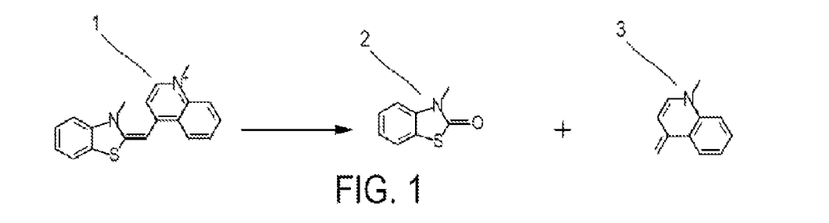
FIG. 1 illustrates the degradation of the molecule of Thiazole Orange (TO) into hydrolysis products.

As illustrated in FIG. 1, in an aqueous medium Thiazole Orange (TO) is unstable and gradually degrades. This degradation results from irreversible splitting of the TO molecule 1 at the level of the methylene bridge into two hydrolysis products, i.e. on the one hand the benzothiazolone moiety (3-methyl-2(3H)-benzothiazolone) 2, and on the other hand a quinoline derivative (1-methyl-4-methylene quinoline) 3.

Figure 2A:
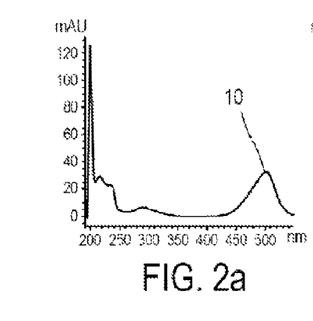
Figure 2B:
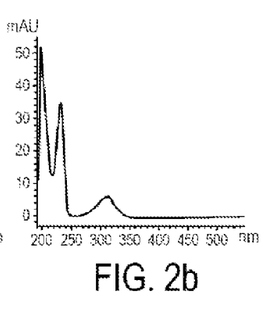
Figure 2C:
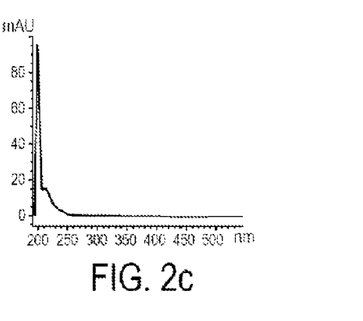

Referring to FIG. 2, TO has a maximum absorption 10 in the visible at a wavelength of the order of 500 nm (FIG. 2a). Now, as illustrated in FIGS. 2b and 2c, none of the two hydrolysis products 1, 2 formed displays absorbance at these wavelengths.

Thus, according to an advantageous aspect of the invention, the degradation of TO may be accurately quantified by measuring the absorbance of the reagent at wavelengths of the order of 500 nm.

It will be recalled that absorbance is defined as a measure of the capacity of a medium to absorb light that passes through it. It is also called optical density or extinction.

The degradation of TO is quicker the higher the temperature, and it is accompanied by a loss of fluorescence of the reagent. Thus, at 22° C., the degradation of Thiazole Orange quantified by its absorbance at 500 nm reaches about 10% after 6 months and may reach 40% in the same time at 35° C.

Figure 3A:
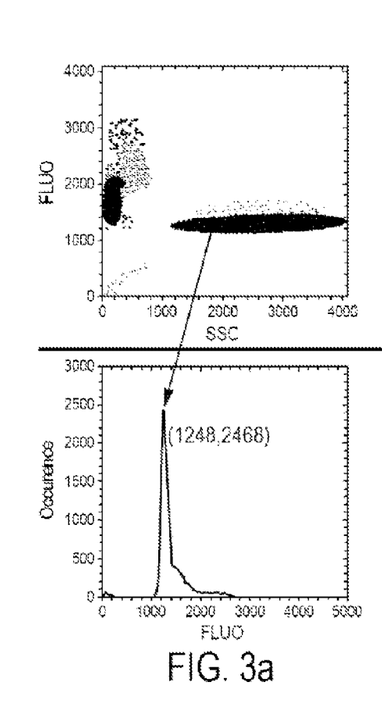
Figure 3B:
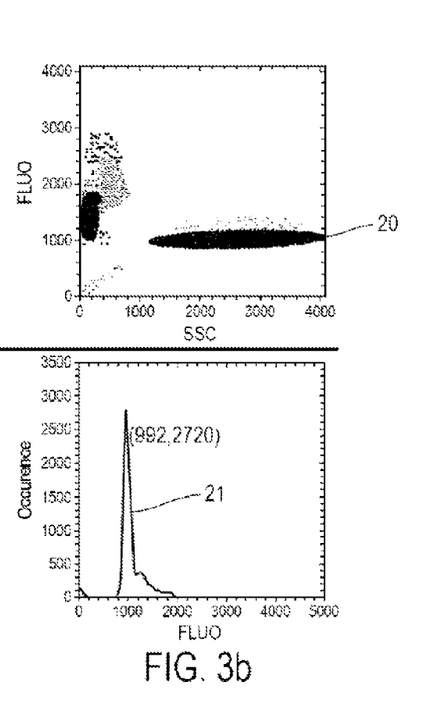

Referring to FIG. 3, when the reagent described in document FR 2 821 428 is used in a flow cytometer such as that described in document WO 2006/024716, degradation of the molecule leads to a change in its optical properties, and notably a loss of fluorescence:

FIG. 3a presents measurements obtained using a hematology analyzer with a reagent used 7 weeks after its date of production, referenced W7;

FIG. 3b presents measurements obtained on the same sample with a reagent used 16 months after its date of production, referenced M16.

In each case, the lower diagram (Occurrence) presents a histogram 21 of the fluorescence measurements obtained on cells labeled with a reagent as described in FR 2 821 428. The fluorescence measurement (FLUO) is a measure of orthogonal fluorescence, carried out in a direction perpendicular to the directions of illumination and flow of cells, which corresponds to the measurement referenced FL1 in document WO 2006/024716. In the upper diagram, each point represents a cell. The points are positioned on axes corresponding, respectively, to the measurements of orthogonal fluorescence (FLUO) and to measurements of orthogonal diffusion (SSC) carried out simultaneously also in a direction perpendicular to the directions of illumination and flow of cells.

The position of the cells in the graph FLUO-SSC makes it possible to identify the granular leukocytes (polynuclear neutrophils and eosinophils), lymphocytes, erythroblasts, monocytes, granular immature leukocytes, and cells with high content of nucleic acids. This classification is detailed in document WO 2006/024716. In particular, the scatter diagram 20 corresponds to the granular cells.

With reagent M16, the fluorescence level of the granular leukocytes is lower by about 256=1258−992 channels (or fluorescence intensity levels FLUO).

In this example, the attenuation of fluorescence is troublesome for three reasons:

the fluorescence level of Thiazole Orange, which is a quantitative measure of the nucleic acids (RNA+DNA), allows differentiation between mature cells and immature cells, as described for example in patent document FR 2 873 813. The immature cells are only present in the blood in the case of pathology, therefore identification of them is crucial in terms of diagnosis. A nonstabilized fluorescence level for a cell line could lead to an increase in false negatives;

in the example in FIG. 3, the biologist sees the fluorescence level of the granular cells appear on channel 992 and not on channel 1248. This thiazole fluorescence must be approximately constant for a given mature cell such as the neutrophil (the genetic material DNA+RNA being constant for a mature normal cell);

it may cause errors in cell classification: here, the population of the erythroblasts has been overestimated since a proportion of the lymphocytes are identified and counted in the zone of the erythroblasts.

Figure 4:
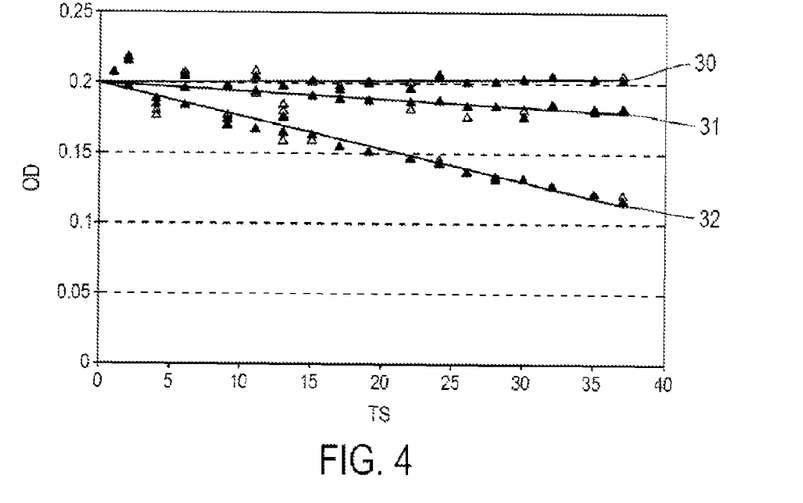
FIG. 4 illustrates the absorbance of a reagent comprising TO as a function of time, in weeks.

As mentioned above, degradation of TO has an effect on the absorbance of the reagent at 500 nm. FIG. 4 presents absorbance measurements (OD) carried out as a function of time (TS), here in weeks, for different temperatures:

curve 30 corresponds to a temperature of 4° C.,
curve 31 corresponds to a temperature of 22° C.,
curve 32 corresponds to a temperature of 35° C.

Therefore the rate of degradation is indeed a function of the temperature of storage of the reagent. Moreover, the fact that the bottles are open or closed does not affect the kinetics, which confirms that this degradation does not result from an oxidation phenomenon.

According to FIG. 4, from a measurement of optical density (OD), it is therefore possible to detect the level of degradation of the reagent caused by the combined effect of time and temperature.

It is very important to emphasize that it is a marker of the temperature and of the thermal conditions of storage: in suitable storage conditions and for a given time, the product will not degrade beyond a certain limit. It is therefore possible to determine a posteriori whether the storage conditions have been respected from the date of manufacture up to the date of use of the product. This deterioration follows the temperature integral and the mechanism of deterioration is irreversible. The measurement of absorption indicates the fraction of Thiazole Orange that has lost its nominal molecular structure.

Advantageously, we discovered that it is possible to construct models for fluorescence correction on this basis.

Figure 5:
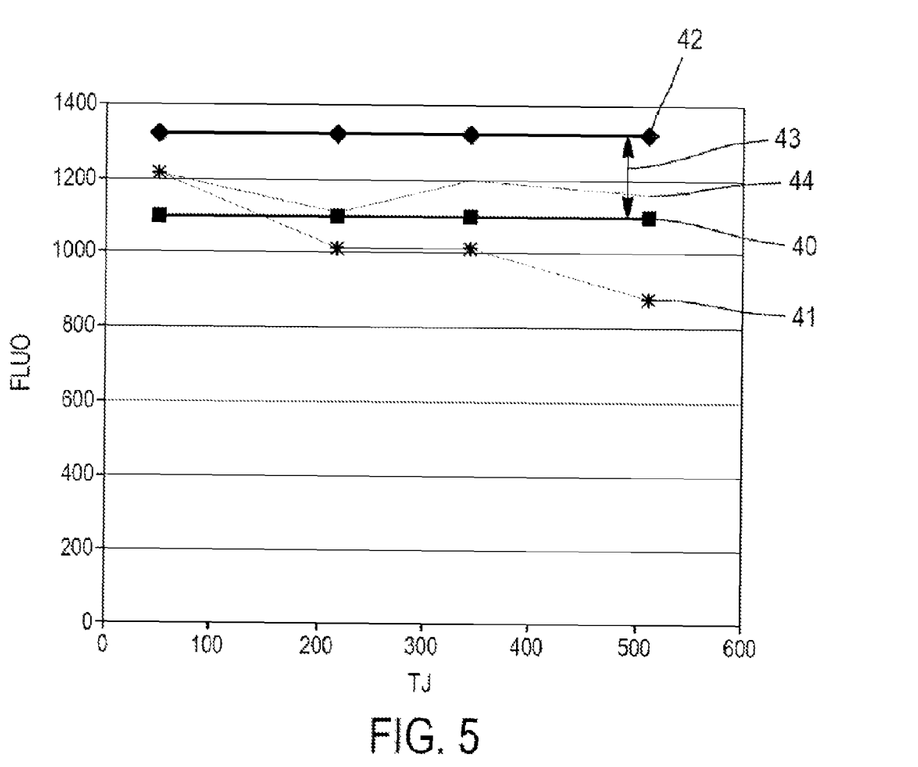
FIG. 5 illustrates the position (in intensity) of the fluorescence peak for neutrophils as a function of the age of the reagent from FIG. 3, in days.

Curve 41 in FIG. 5 shows the evolution of the position (or intensity) of the modal peak of fluorescence (FLUO) of the granular leukocytes as a function of the age of the reagent. The crosses correspond respectively to dates of use at 7 weeks, 6 months, 12 months and 16 months from the date of manufacture of the reagent. The horizontal axis (TJ) is in days.

As can be seen, the fluorescence levels decrease as a function of time monotonically, but without it appearing obvious at first glance to determine the law of decrease accurately.

Models for fluorescence correction have therefore been elaborated in the context of the invention.

First Correction Model

According to the first correction model, the method for compensating for the degradation of the reagent comprises the following steps.

First, the initial optical density of the reagent is measured, taken separately on its date of manufacture, therefore without degradation. This value is denoted OD(0). This measurement may be carried out for example during acceptance testing of the reagent, or during its manufacture.

During use of the analyzer, measurements of the current optical density OD(t) are performed for the reagent taken separately at a given time point t. These measurements are preferably performed at a time point t close to the time point when the fluorescence measurements, denoted FLUOm(t), are taken, i.e. in the same day or the same week. They may be carried out for example during a maintenance cycle or at daily or weekly start-up of the blood analyzer.

To perform the correction, the following ratio is calculated:

$$K(t)=OD(0)/OD(t).$$

This ratio K(t) makes it possible to compare OD(t) in relation to the nominal value of the optical density of the undegraded reagent OD(0).

The ratio K(t) gives a coefficient (greater than one) that is used as a coefficient for correcting the fluorescence signal measured on the date t of use of the reagent, FLUOm(t), which allows calculation of the corrected fluorescence level $$FLUOc(t)=K(t) \times FLUOm(t).$$

The effect of this first correction model is illustrated in FIG. 5: the points of curve 44 correspond to the measured values of the fluorescence peak of the granular cells of curve 41 multiplied by the correction coefficient K.

It can be seen that this operation allows the fluorescence intensity to be replaced between the two tolerance limits, high 42 and low 43, which allow the algorithm to accurately identify this population of granular cells.

This first correction model is based on a hypothesis of proportionality between the changes in optical density from the origin, and the changes in fluorescence intensity, also from the origin. It has the advantage of being simple and of not requiring any previous analysis of the behavior of the reagent over time.

The method may be generalized to a reagent comprising several fluorescent compounds, with absorption peaks at different wavelengths and optionally different degradation characteristics.

In this case, it is possible to:
- carry out measurements of initial optical densities $ODi(0)$ and measurements of current optical densities $ODi(t)$ at several groups of wavelengths $\lambda i$,
- calculate ratios $Ki(t)=ODi(0)/ODi(t)$ at these wavelengths, and
- apply separate corrections to the different fluorescence measurements $FLUOci(t)=Ki(t) \times FLUOmi(t)$ corresponding to the different fluorescent compounds.

Second Correction Model

This correction model is based on prior determination of a model of degradation of the reagent. This determination may be carried out starting from experimental measurements of absorbance OD and of fluorescence levels FLUO on reference cells, carried out during aging of the reagent.

The model of degradation makes it possible to express a change in fluorescence level $\Delta FLUO$ as a function of a change in optical density of the reagent $\Delta OD$:

$$\Delta FLUO=f(\Delta OD).$$

In general, the model of degradation may be expressed in the form of a linear coefficient:

$$\alpha=\Delta FLUO/\Delta OD.$$

Next, in the same way as for the first correction model, the initial optical density of the reagent is measured, taken separately on its date of manufacture, therefore without degradation. This value is denoted OD(0). This measurement may be carried out for example during acceptance testing of the reagent, or during its manufacture.

During use of the analyzer, measurements of the current optical density OD(t) are performed for the reagent taken separately at a given time point t. These measurements are preferably performed at a time point t close to the time point when the fluorescence measurements, denoted FLUOm(t), are taken, i.e. in the same day or the same week. They may be carried out for example during a maintenance cycle or at daily or weekly start-up of the blood analyzer.

The number of fluorescence channels (or levels) lost is calculated:

$$CP(t)=f(OD(0)-OD(t)),$$

or, in the case of a linear coefficient:

$$CP(t)=(OD(0)-OD(t)) \times \alpha.$$

A corrective gain can then be calculated:

$$GC(t)=<FLUO(t)>/(<FLUO(t)>-CP(t)).$$

The quantity $<FLUO(t)>$ is a reference fluorescence value which may be, nonexhaustively, a median or mean value of the measurements, or a value corresponding to a particular population of cells.

The corrective gain GC(t) is then applied to the fluorescence signal measured on the date t of use of the reagent, FLUOm(t), which allows the corrected fluorescence level to be calculated, $$FLUOc(t)=GC(t) \times FLUOm(t).$$

The method may be generalized to the measurement of several optical densities denoted ODi (i is between 1 and n) for groups of wavelengths in the range from $\lambda i$ to $\lambda n$.

Then n functions denoted $fi(\Delta ODi)$ may be determined, allowing separate corrections to be calculated for different fluorescence wavelengths. These corrections are written in the form:

$$CPi(t)=fi(ODi(0)-ODi(t)), i \text{ being between 1 and } n.$$

As nonlimiting examples, a reagent consisting of two fluorescent compounds may be based on Thiazole Orange and the compound Hoechst® 33342 which is a stain with high DNA affinity. One or more fluorescent compounds may also be selected from the following nonexhaustive list: SYTOX Green, Vybrant series, YOYO-1, SYTO series, Hoechst series, Acridine Orange or SYBR Green 1.

An example of application of the second correction model to Thiazole Orange will now be described in greater detail.

The measurements of optical density are performed in a spectrophotometry measurement chamber. The measurement cell is traversed by a light beam from a light-emitting diode of the NICHIA® NSP590S type (green with a blue tinge), whose central emission wavelength is 501 nm for an intensity of i=30 mA. In acceptance testing, an OSRAM® BPW21 photodiode is used, which is suitable for applications between 350 nm and 820 nm, with spectral sensitivity of 0.34 A/W at 550 nm.

In order to construct an accurate correction model, measurements of optical density were performed for reagents aged respectively 3 weeks (W3), 5 weeks (W5), 13 weeks (W13), 32 weeks (W32), 52 weeks (W52) and 77 weeks (W77).

It is considered that the value of optical density at t=0 denoted OD(0) is that corresponding to W3.

The difference ΔOD(t) between the initial optical density OD(0) and each of the optical densities OD(t) measured over time is deduced from this.

Here are the results:

| Weeks | days | OD | measured ΔOD |
|---|---|---|---|
| 3 | 21 | 0.2943 | 0 |
| 5 | 35 | 0.2956 | −0.0013 |
| 13 | 91 | 0.2835 | 0.0108 |
| 32 | 224 | 0.2401 | 0.0542 |
| 52 | 364 | 0.2197 | 0.0746 |
| 77 | 539 | 0.1936 | 0.1007 |

An interpolation model may thus be constructed, allowing ΔOD to be calculated at any time point:

$$\Delta OD = -2 \cdot 10^{-7} \, t^2 + 0.003 \, t - 0.0104, \text{ with } t \text{ in days.}$$

This model displays a very good correlation coefficient ($R^2 = 0.9918$).

Fluorescence measurements were moreover carried out on three fresh blood samples. For each fresh blood sample, the mean value of the fluorescence intensity $<FLUO(t)>$ of the neutrophils was calculated.

The neutrophils were selected because they give a readily identifiable scatter diagram with little dispersion during the measurements (scatter diagram 20 in FIG. 3). It is known that the mean value of the fluorescence intensity for the fresh blood samples must be adjusted to 1100 channels (of intensity) for a temperature of 35°.

It is thus possible to evaluate, for these fresh blood samples, the loss of fluorescence (measured ΔFLUO) as a function of the age of the reagent. The results are as follows:

| age of the reagent | age of the reagent in days | calculated ΔOD | measured ΔFLUO |
|---|---|---|---|
| W7 | 49 | 0.0043 | 30 |
| M7 | 212 | 0.0477 | 150 |
| M11 | 334 | 0.0727 | 162 |
| M16 | 486 | 0.0956 | 286 |

The change in optical density ΔOD is calculated with the interpolation model.

Figure 6:
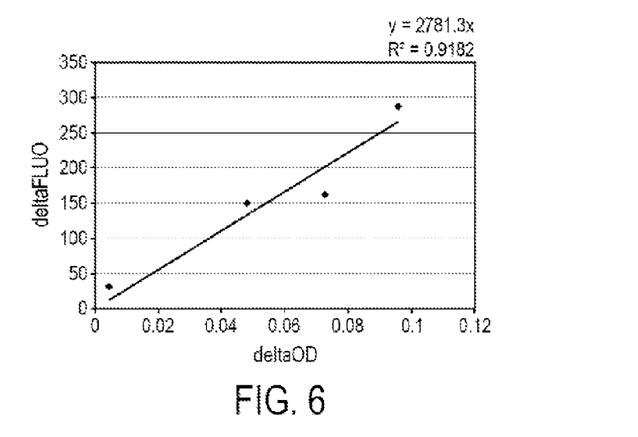
FIG. 6 presents measurements of the change in fluorescence level as a function of changes in optical density.

Referring to FIG. 6, therefore the correlation between the changes in fluorescence levels and the changes in optical density is established, and the coefficient α=ΔFLUO/ΔOD of the model of degradation can be deduced from this.

Here we obtain α=3000.

Compensation of the measurements is carried out as follows.

For each reagent, the optical density OD(0) should be measured as close as possible to its date of production. In our experiment, OD(0)=0.2385.

Then, a measurement of optical density OD(t) of each of the reagents is performed prior to passage of a series of samples.

The number of lost fluorescence channels is calculated:

$$CP(t) = (OD(0) - OD(t)) \times 3000.$$

It is considered that this number of lost channels is equivalent to the loss on the mean value of fluorescence intensity of the neutrophils $<FLUO(t)>$.

The mean fluorescence intensity of the neutrophils is 1100; a corrective gain for the set of cells is deduced from this:

$$GC(t) = 1100/(1100 - CP(t)).$$

FIG. 7 illustrates an example of compensation. In FIGS. 7a to 7f, each point represents a cell. The points are positioned according to axes corresponding, respectively, on the abscissa to measurements of orthogonal diffusion (SSC), and on the ordinate to measurements of orthogonal fluorescence (FLUO), carried out simultaneously and in a direction perpendicular to the directions of illumination and cell flow.

Figure 7A:
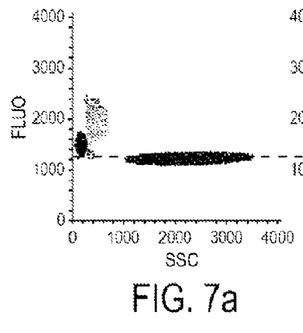
FIGS. 7a to 7f illustrate measurement results obtained with the method according to the invention.
Figure 7B:
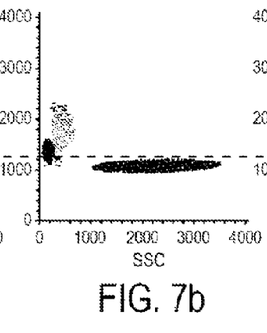
Figure 7C:
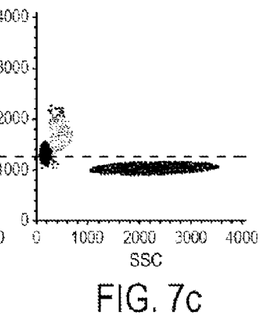

FIGS. 7a, 7b and 7c present measurements without compensation, with a reagent respectively on leaving production, aged 9 months (M9) and aged 13 months (M13). A displacement of the fluorescence levels can clearly be seen.

Figure 7D:
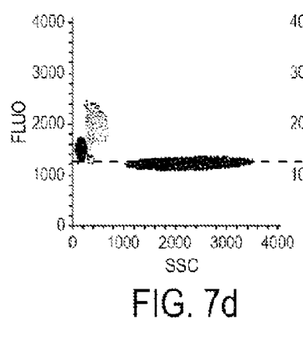
Figure 7E:
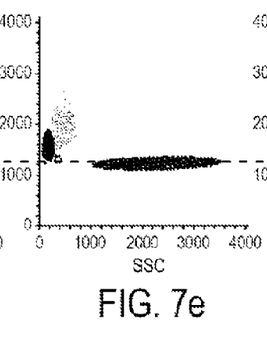
Figure 7F:
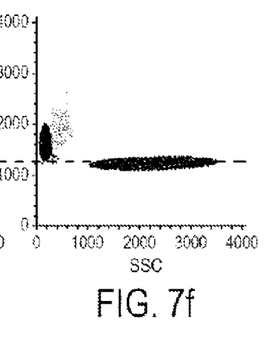

FIGS. 7d, 7e and 7f present measurements with the compensation as described above, with a reagent respectively on leaving production, aged 9 months (M9) and aged 13 months (M13). The corrected fluorescence levels remain effectively constant.

The methods of compensation according to the invention are notably very useful for the blood samples on which the use of fixed thresholds is indispensable (for example if there are too few cells, or no labeled population). In fact, the use of fixed thresholds requires being extremely precise with the fluorescence, since the fluorescence is the basis for determining the degree of maturity of the cells and therefore detection of a possible pathological condition. Thus, uncertainty regarding the fluorescence of the cells might for example lead to non-detection of blast cells. This method of compensation is therefore indispensable for avoiding false negatives.

The method according to the invention can easily be integrated in a biological analysis device, or a blood analyzer.

Its application can be automated extensively by providing the device with a cell for measurement by spectrophotometry, in which the measurements of optical density of the reagent or reagents are carried out.

For taking measurements at different wavelengths, it may be advantageous to use a polychromatic light source and a photoreceptor provided with an optical filtering system allowing measurement of the optical densities at the various central wavelengths λi (i is between 1 and n).

An example of application of the method according to the invention in a biological analysis device or blood analyzer will now be presented.

Figure 8:
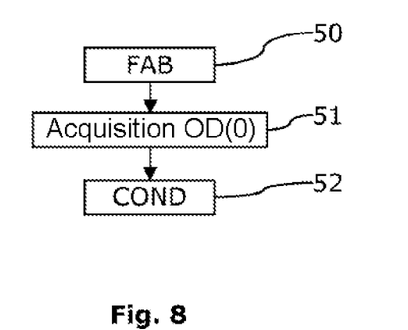
FIG. 8 illustrates a sequence of operations carried out during manufacture of a reagent.

Referring to FIG. 8, first, the reagent is produced (step 50) and then packaged in containers such as bottles (step 52).

As explained above, the method according to the invention further comprises a step 51 of measurement of the initial optical density OD(0) of the reagent, which is carried out before or during packaging 52.

The value of the measured initial optical density OD(0) is stored for example in a RFID tag fixed on the container, for later use.

Figure 9:
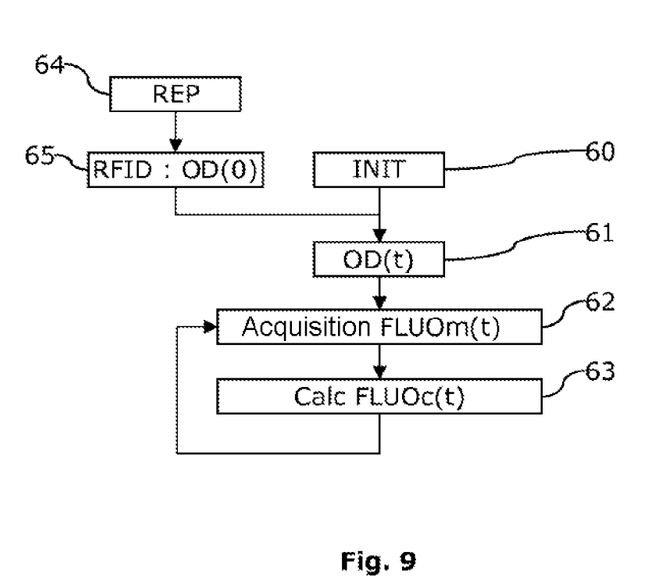
FIG. 9 illustrates a sequence of operations carried out in a device for biological analysis or blood analysis.

Referring to FIG. 9, secondly, the bottles of reagent are inserted (step 64) in a biological analysis device or blood analyzer, for the purpose of using the reagent. The RFID tag is then read (step 65) and the value of initial optical density OD(0) of the reagent contained in this bottle is stored in the device.

Usually, execution of measurements with a biological analysis device or blood analyzer requires a preliminary initialization step 60, which is carried out for example daily. This initialization step 60 comprises usual operations of monitoring, control, rinsing, etc., to ready the device for performing measurements.

According to the invention, a step 61 of measuring the current optical density OD(t) of the reagent is then also carried out. A value of current optical density OD(t) is thus obtained, which is used for correcting the measurements until execution of a new initialization step 60, or until replacement 64 of the bottle of reagent if the latter occurs first.

In case of replacement 64 of a bottle of reagent, measurement 61 of the current optical density OD(t) of the fresh reagent is carried out prior to use.

Measurement cycles may then be carried out on biological samples or blood samples.

These measurement cycles comprise:
acquisition 62 of fluorescence signal measurements FLUOm(t);
correction 63 of the effects of degradation of the reagent, to obtain corrected values FLUOc(t). The corrected values FLUOc(t) are calculated according to the correction models described above, using the stored values of initial optical density OD(0) and of current optical density OD(t).

Owing to the periodical repetition of the initialization steps 60, the measurements 61 of current optical density OD(t) can be regarded as having been carried out at time points sufficiently close to the time points when the fluorescence measurements FLUOm(t) are carried out.

Of course, the invention is not limited to the examples that have just been described, and many adjustments may be made to these examples while remaining within the scope of the invention.

The invention claimed is:

1. A method for identifying particles by compensating for the decomposition of a stored aqueous phase reagent that comprises at least one fluorescent compound comprising measuring fluorescence level FLUOm(t) on particles labelled with said reagent:
measuring the absorbance of a solution comprising said reagent with at least one wavelength at a time point t, wherein t is measured at a point close to the measurements of the fluorescence level FLUOm(t), to obtain at least one current optical density OD(t) of the reagent, and,
calculating a correction of the measurements of the fluorescence level using said current optical density or densities OD(t) and at least one initial optical density OD(0) of the degradation-free reagent
calculating a ratio K(t) corresponding to the ratio of an initial optical density OD(0) to a current optical density OD(t), and
calculating corrected fluorescence levels FLUOc(t) by multiplying the fluorescence levels FLUOm(t) measured around the measurement time point t on particles labelled with the reagent, by the ratio K(t).

2. The method according to claim 1, wherein the at least one fluorescent compound is a polymethine type.

3. The method according to claim 1 wherein the reagent comprises Thiazole Orange.

4. The method according to claim 1, further comprising:
measuring initial optical densities ODi(0) and current optical densities ODi(t) at several wavelengths λi,
calculating ratios Ki(t) at said wavelengths λi, and
calculating corrected fluorescence levels FLUOci(t) at said wavelengths λi.

5. The method according to claim 1 further comprising:
establishing a degradation model before initiating the method by obtaining a relation between changes in fluorescence level ΔFLUO on reference particles and changes in the optical density of the reagent ΔOD due to its degradation, and
calculating a number of lost fluorescence channels CP(t), from measurements of current optical density OD(t), initial optical density OD(0), and from said the degradation model.

6. The method according to claim 5, further comprising:
determining before initiating the method, a degradation model in the form of a coefficient α corresponding to a ratio of changes in fluorescence level ΔFLUO to changes in optical density of the reagent ΔOD,
calculating a number of lost fluorescence channels CP(t), in the form of a difference between the current optical density OD(t) and the initial optical density OD(0), multiplied by the coefficient α,
obtaining a reference fluorescence value <FLUO(t)> statistically representative of the measured fluorescence levels FLUOm(t),
calculating a corrective gain GC(t) corresponding to a reference fluorescence value <FLUO(t)> divided by a difference between said reference fluorescence value <FLUO(t)> and the number of lost fluorescence channels CP(t), and
calculating corrected fluorescence levels FLUOc(t) by multiplying the fluorescence levels FLUOm(t) measured at a measurement time point t on particles labeled with the reagent, by the corrective gain GC(t).

7. The method according to claim 5 further comprising obtaining a plurality of degradation models from measurements of optical densities at several wavelengths.

8. A device comprising means for measuring fluorescence level on particles labeled with a reagent
means for performing absorbance measurements at at least one wavelength of a solution comprising the reagent, at a time point t close to that of said measurements of the fluorescence level, to determine at least one current optical density OD(t) of the reagent, and
means for calculating a correction of the fluorescence levels measurements using said current optical density or densities OD(t) and at least one initial optical density OD(0) of the degradation-free reagent.

9. The device according to claim 8, further comprising a cell for measurement by spectrophotometry.

10. The device according to claim 9, wherein the cell comprises a polychromatic light source and a photoreceptor that includes an optical filtering system configured to measure the optical densities the various central wavelengths λi.

11. The device according to claim 8, further comprising a hematology analyzer.

* * * * *